(12) United States Patent
Kim et al.

(10) Patent No.: US 10,179,570 B2
(45) Date of Patent: Jan. 15, 2019

(54) TOTAL-REFLECTION-TYPE RAIN SENSOR USING MIRROR

(71) Applicants: ACCENDO MOTION RESEARCH CO., LTD, Wanju-Gun, Jeollabuk-do (KR); DREAMTECH CO., LTD, Seongnam-si, Gyeonggi-do (KR)

(72) Inventors: Young-Ho Kim, Yongin-si (KR); Jin Sang Lee, Seoul (KR); Yong Pyo Hong, Iksan-si (KR); Nam Joon Yoo, Iksan-si (KR)

(73) Assignees: ACCENDO MOTION RESEARCH CO., LTD, Wanju-Gun, Jeollabuk-do (KR); DREAMTECH CO., LTD, Seongnam-si, Gyeonggi-do (KR)

( * ) Notice: Subject to any disclaimer, the term of this patent is extended or adjusted under 35 U.S.C. 154(b) by 105 days.

(21) Appl. No.: 15/315,191

(22) PCT Filed: May 30, 2014

(86) PCT No.: PCT/KR2014/004871
§ 371 (c)(1),
(2) Date: Nov. 30, 2016

(87) PCT Pub. No.: WO2015/182803
PCT Pub. Date: Dec. 3, 2015

(65) Prior Publication Data
US 2017/0190319 A1    Jul. 6, 2017

(30) Foreign Application Priority Data

May 30, 2014    (KR) ........................ 10-2014-0066534

(51) Int. Cl.
*B60S 1/08*  (2006.01)
*G01J 1/42*  (2006.01)
*G01N 21/17*  (2006.01)
*G01W 1/14*  (2006.01)

(52) U.S. Cl.
CPC .......... *B60S 1/0837* (2013.01); *B60S 1/0822* (2013.01); *B60S 1/0844* (2013.01); *G01J 1/42* (2013.01);
(Continued)

(58) Field of Classification Search
CPC .... B60S 1/0837; B60S 1/0833; B60S 1/0818; B60S 1/0844; G01N 2021/435
See application file for complete search history.

(56) References Cited

U.S. PATENT DOCUMENTS

2002/0033459 A1* 3/2002 Graves .................. B60S 1/0822
                                                               250/573
2005/0035926 A1* 2/2005 Takenaga .............. B60S 1/0818
                                                               345/8

(Continued)

FOREIGN PATENT DOCUMENTS

CN    101819144 A    9/2010
DE    197 13 909 C1  11/1998
(Continued)

OTHER PUBLICATIONS

The extended European search report dated May 19, 2017 in connection with the counterpart European Patent Application No. 14893288.2.

(Continued)

*Primary Examiner* — Thanh Luu
(74) *Attorney, Agent, or Firm* — Hauptman Ham, LLP

(57) ABSTRACT

The present invention relates to a total reflection type rain sensor using a mirror, which is attached to a glass of a vehicle to detect raindrops falling onto the glass of the vehicle and outputs a signal capable of controlling speed and cycle of a wiper of the vehicle according to the amount and falling frequency of raindrops detected.

20 Claims, 9 Drawing Sheets

(52) U.S. Cl.
CPC .......... *G01N 21/1717* (2013.01); *G01W 1/14* (2013.01); *B60S 1/0833* (2013.01); *G01J 2001/4238* (2013.01); *G01N 2021/1725* (2013.01); *G01N 2021/1742* (2013.01)

(56) References Cited

U.S. PATENT DOCUMENTS

| | | | |
|---|---|---|---|
| 2005/0082499 A1 | 4/2005 | Graves et al. | |
| 2006/0202654 A1 | 9/2006 | Michiyama | |
| 2006/0215164 A1* | 9/2006 | Takata | B60S 1/0822 356/445 |
| 2007/0114369 A1* | 5/2007 | Tarui | G01N 21/274 250/227.25 |

FOREIGN PATENT DOCUMENTS

| | | |
|---|---|---|
| JP | 10-300861 A | 11/1998 |
| JP | 11-34801 A | 2/1999 |
| JP | 11-509932 A | 8/1999 |
| KR | 10-2006-0099399 A | 9/2006 |
| KR | 10-2010-0010752 A | 2/2010 |
| KR | 10-2012-0012269 A | 2/2012 |

OTHER PUBLICATIONS

International Search Report dated Jan. 20, 2015 corresponding to International Application No. PCT/KR2014/004871.
Chinese Office Action dated May 3, 2018 for corresponding Korean Application No. 201480079440.9.

* cited by examiner (a)

(b)

(a)

(b)

(c)

TOTAL-REFLECTION-TYPE RAIN SENSOR USING MIRROR

CROSS REFERENCE TO RELATED APPLICATION

This application claims the priority of Korean Patent Application No. 10-2014-0066534 filed on May 30, 2014, in the Korean Intellectual Property Office, the disclosure of which is incorporated herein by reference. Further, this application is the National Phase application of International Application No. PCT/KR2014/004871 filed May 30, 2014, which designates the United States and was published in Korean.

TECHNICAL FIELD

The present invention relates to a total reflection type rain sensor using a mirror, which is attached to a glass of a vehicle to detect raindrops falling onto the glass of the vehicle and outputs a signal capable of controlling speed and cycle of a wiper of the vehicle based on an amount and falling frequency of raindrops detected.

More specifically, the present invention relates to a total reflection type rain sensor using a mirror, comprising a light emitting unit, an adhering portion, a light receiving unit and a control unit, the rain sensor being attached to a glass of a vehicle to detect raindrops falling onto the glass of the vehicle, wherein the light emitting unit emits light to be incident on the glass of the vehicle, the light receiving unit receives the light that is emitted from the light emitting unit and then reflected totally from the glass of the vehicle, the adhering portion allowing the rain sensor to be attached to the glass of the vehicle, and the control unit receives a signal output from the light receiving unit that receives the light and actuates the wiper of the vehicle.

The present invention relates to a total reflection type rain sensor using a mirror wherein operation speed and cycle of the wiper of the vehicle can be controlled by the control unit which receives a signal of the light receiving unit which receives light reflected totally at different amounts depending on the amount of raindrops.

The present invention relates to a total reflection type rain sensor using a mirror wherein the rain sensor stores a predetermined threshold value for an amount of raindrops that allows operation of the wiper of the vehicle to initiate and outputs a signal for initiating operation of the wiper of the vehicle when the amount of raindrops detected exceeds the threshold value.

The present invention relates to a total reflection type rain sensor using a mirror wherein a light emitting parabolic mirror module allows the light emitted from the light emitting unit to be reflected therefrom in such a manner that (a) wavelengths of the light can be maintained in parallel with each other and (b) the light is incident at an angle that allows the light to be reflected totally from the glass of the vehicle.

The present invention relates to a total reflection type rain sensor using a mirror wherein the light emitting unit comprises a plurality of light emitting units so that a plurality of detection areas for detecting raindrops are formed.

The present invention relates a total reflection type rain sensor using a mirror wherein a light emitting sawtooth-shaped rotary prism unit (a) allows the light reflected from and adjusted by the light emitting parabolic mirror module to be held thereby until the light is incident on the glass of the vehicle and (b) can rotate a direction of the light to be received by a single light receiving unit in case where the light receiving unit comprises a plurality of light receiving units.

The present invention relates to a total reflection type rain sensor using a mirror wherein a light receiving sawtooth-shaped rotary prism unit that is symmetrical with the light emitting sawtooth-shaped rotary prism unit allows the light reflected from the glass of the vehicle to be deviated toward and then received by the light receiving module.

BACKGROUND ART

Wipers of a vehicle are means for securing a field of view of a driver and thus helping safe driving by removing raindrops falling on glasses of the vehicle, which are installed at the front and rear of the driver's seat, when the vehicle is running in the rain.

Such a wiper is configured to operate in response to switch manipulation of a driver when the vehicle is running in the rain.

In recent years, a technology has been developed to automatically operate the wiper for the sake of driving convenience of the driver without any necessity for the driver to manipulate the wiper separately during driving in the rain.

This technology can be achieved through a rain sensor that detects raindrops falling on the glass of the vehicle.

In this case, the rain sensor detects raindrops when the raindrops fall on the glass of the vehicle and then actuates the wiper, while it stops operation of the wiper when the raindrops are not detected.

Since such a rain sensor is configured to operate the wiper when raindrops are detected from the glass of the vehicle, the following problems may occur.

First, there is a problem that the wiper is operated even when raindrops fall at such a degree that there is no need to operate the wiper.

In particular, as technology has been developed in recent years, it is possible to automatically remove raindrops by spraying a specific liquid on the glass of the vehicle, which may cause raindrops falling on the glass of the vehicle to be automatically removed due to airflow generated during running of the vehicle. In this case, operating the wiper even when raindrops fall at such a degree that there is no need to operate the wiper will consume unnecessary power.

Second, since the rain sensor in turns uses electric power of the vehicle, there is a problem that accumulation of unnecessary operation of the wiper may affect discharge of the vehicle.

On the other hand, as a technology related to a rain sensor, a prism mediated type rain sensor is disclosed in Korean Laid-Open Patent Publication No. 10-2010-0010752.

The above document discloses a rain sensor to detect amount of rain more accurately by eliminating parameters unnecessary for infrared ray detection, wherein the rain sensor is configured to use a prism to reflect and refract infrared ray beam which is generated from an infrared ray LED and then emitted to a windshield glass of a vehicle and allow the infrared ray beam to be received from the windshield glass of the vehicle through a infrared ray filter and the prism again so that a structure for collecting light is simplified.

However, since the above document only discloses the structure of the rain sensor and does not disclose any configuration associated with the wiper of the vehicle, it cannot solve the problems as mentioned above.

Further, Korean Laid-Open Patent Publication No. 10-2012-0012269 discloses a device for detecting raindrops.

This document discloses a device for detecting raindrops that is capable of controlling operation of a wiper of a vehicle by detecting an amount of the raindrops, wherein the device comprises a light guide unit which is in close contact with a surface of a glass of the vehicle and allows incident guide light to be totally reflected from the surface of the glass, a light emitting unit provided at an incident side of the light guide unit to emit light source, and a light receiving unit provided at an output side of the light guide unit to filter a predetermined narrow band light from the light received.

The document also describes that a time period of operation of the wiper can be adjusted according to the amount of rainfall using information of raindrops detection from the device for detecting raindrops.

However, this document also describes only the device for detecting raindrops for operation of the wiper and cannot solve the problem that unnecessary operation of the wiper must be minimized.

Therefore, there is a need to develop a technology capable of detecting raindrops falling on a glass of a vehicle through a rain sensor and minimizing unnecessary operation of a wiper depending on an amount of raindrops detected.

In addition, there is a need to develop a technology capable of allowing the emitted light to be easily and totally reflected from a glass of a vehicle and assisting to receive the light totally reflected from the glass of the vehicle.

Furthermore, there is a need to develop a technology that can broaden a detection area for detecting raindrops falling on a glass of a vehicle.

DISCLOSURE

Technical Problem

The present invention has been made in an effort to meet the needs described above. An object of the present invention is to provide a total reflection type rain sensor using a mirror, which is attached to a glass of a vehicle to detect raindrops falling on the glass of the vehicle and output a signal capable of controlling speed and cycle of a wiper of the vehicle according to the amount and falling frequency of raindrops detected, wherein the rain sensor comprises a light emitting unit for emitting light to be incident on the glass of the vehicle; a light receiving unit for receiving the light that is emitted from the light emitting unit and then reflected totally from the glass of the vehicle; an adhering portion allowing the rain sensor to be attached to the glass of the vehicle; and a control unit for receiving a signal output from the light receiving unit that receives the light and actuating the wiper of the vehicle.

Another object of the present invention is to provide a total reflection type rain sensor using a mirror wherein operation speed and cycle of the wiper of the vehicle can be controlled by the control unit which receives a signal of the light receiving unit which receives light reflected totally at different amounts depending on the amount of raindrops.

Still another object of the present invention is to provide a total reflection type rain sensor using a mirror wherein the rain sensor stores a predetermined threshold value for an amount of raindrops that allows operation of the wiper of the vehicle to initiate and outputs a signal for initiating operation of the wiper of the vehicle when the amount of raindrops detected exceeds the threshold value.

Yet another object of the present invention is to provide a total reflection type rain sensor using a mirror wherein a light emitting parabolic mirror module allows the light emitted from the light emitting unit to be reflected therefrom in such a manner that (a) wavelengths of the light can be maintained in parallel with each other and (b) the light is incident at an angle that allows the light to be reflected totally from the glass of the vehicle.

Still yet another object of the present invention is to provide a total reflection type rain sensor using a mirror wherein the light emitting unit comprises a plurality of light emitting units so that a plurality of detection areas for detecting raindrops are formed.

A further object of the present invention is to provide a total reflection type rain sensor using a mirror wherein a light emitting sawtooth-shaped rotary prism unit (a) allows the light reflected from and adjusted by the light emitting parabolic mirror module to be held thereby until the light is incident on the glass of the vehicle and (b) can rotate a direction of the light to be received by a single light receiving unit in case where the light receiving unit comprises a plurality of light receiving units.

Another further object of the present invention is to provide a total reflection type rain sensor using a mirror wherein a light receiving sawtooth-shaped rotary prism unit that is symmetrical with the light emitting sawtooth-shaped rotary prism unit allows the light reflected from the glass of the vehicle to be deviated toward and then received by the light receiving module.

Technical Solution

According to an aspect of the present invention for accomplishing the objects described above, there is provided a total reflection type rain sensor using a mirror, comprising a light emitting unit, an adhering portion, a light receiving unit and a control unit, the rain sensor being attached to a glass of a vehicle to detect raindrops falling onto the glass of the vehicle, wherein the light receiving unit receives light that is emitted from the light emitting unit and then reflected totally from the glass of the vehicle and outputs a signal regarding an amount of the light received; and the control unit outputs to the vehicle a control signal capable of initiating operation of a wiper of the vehicle in such a manner that the control unit receives and analyzes the signal of the light receiving unit and as a result of the analysis, outputs the control signal when the amount of the raindrops exceeds a threshold value predetermined and stored therein.

Advantageous Effects

A total reflection type rain sensor using a mirror according to the present invention detects raindrops falling on a glass of a vehicle and outputs a control signal for initiating operation of a wiper when an amount of the raindrops exceeds a predetermined threshold value stored therein, so that it has a remarkable effect that unnecessary operation of the wiper can be minimized.

In addition, the present invention has a remarkable effect that accuracy of deviation of the light emitting and light receiving sawtooth-shaped rotary prism units can be enhanced because the light emitted from the light emitting unit is reflected through the light emitting parabolic mirror module and wavelengths of the light can be reflected in parallel.

Further, the present invention has a remarkable effect that a more precise total reflection can be induced because when the light emitted from the light emitting unit is incident on the glass of the vehicle through the light emitting parabolic mirror module, it is possible for the light to be incident at an angle beyond a threshold angle for total reflection.

Further, the present invention has a remarkable effect that accuracy of receipt of light can be enhanced because the light receiving sawtooth-shaped rotary prism unit is formed with prisms formed in a direction that is symmetrical with prisms of the light emitting sawtooth-shaped rotary prism unit so that (a) the light whose angle is converted can be maintained through the light emitting parabolic mirror module and (b) a direction of light can be rotated such that the light emitted from the light emitting unit can be received by a single light receiving unit.

BEST MODE

Figure 1:
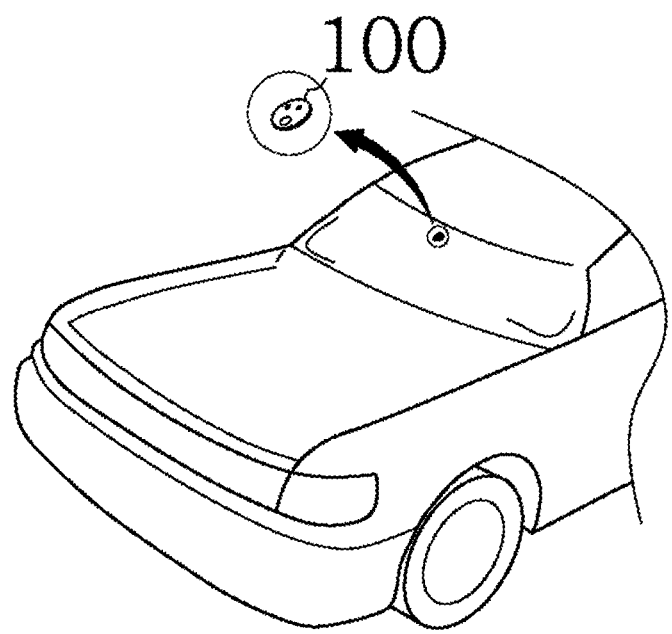
FIG. 1 illustrates an example where a total reflection type rain sensor using a mirror according to the present invention is attached to a vehicle.

It should be understood that terms or words used in the specification and the appended claims should not be construed as being limited to commonly employed meanings or dictionary definitions, but interpreted based on meanings and concepts corresponding to the technical idea of the invention, on the basis of the principle that inventors are allowed to define terms appropriately for the best explanation of their invention.

Accordingly, the embodiments described in the present specification and the construction shown in the drawings are nothing but one preferred embodiment of the present invention, and it does not cover all the technical ideas of the invention. Thus, it should be understood that various changes and modifications may be made at the time of filing the present application.

Hereinafter, prior to describing the present disclosure with reference to the accompanying drawings, it is noted that matters not required to reveal the gist of the present disclosure, i.e., well-known configurations that can be added apparently by those skilled in the art will be neither illustrated nor described in detail.

The present invention relates to a total reflection type rain sensor using a mirror, which is attached to a glass of a vehicle to detect raindrops falling onto the glass of the vehicle and outputs a signal capable of controlling speed and cycle of a wiper of the vehicle according to the amount and falling frequency of raindrops detected.

An exemplary example that a total reflection type rain sensor using a mirror according to the present invention is attached to a glass of a vehicle will be described with reference to FIG. 1 of the accompanying drawings.

FIG. 1 illustrates an example where a total reflection type rain sensor using a mirror according to the present invention is attached to a vehicle.

That is, as shown in FIG. 1, the rain sensor 100 can be attached to a windshield glass of a vehicle to detect raindrop falling on the windshield glass. In this case, it is appreciated that matters falling on the windshield glass include not only raindrops but also any liquid substance similar to raindrops.

FIG. 1 of the accompanying drawings shows the rain sensor 100 as being attached to the windshield glass of the vehicle. However, the scope of the invention cannot be limited or narrowed by the drawings. Therefore, it is noted that the rain sensor may be attached to not only the windshield glass of the vehicle but also any glass (e.g., rear glass) that can be equipped with a wiper among glasses of the vehicle.

In particular, since the rain sensor 100 is attached to the glass of the vehicle, it may be designed to conform to the curvature of a surface of the glass of the vehicle. However, as the rain sensor 100 according to the present invention is designed to be compact, it can be used by simply attaching to the glass of the vehicle without need to design it to conform to the curvature of the surface of the glass of the vehicle.

Preferably, the rain sensor 100 can be designed to have a radius of 17.5 mm and a height of 7.0 mm.

An exemplary total reflection type rain sensor using a mirror according to the present invention will be described below with reference to FIGS. 2 and 3 of the accompanying drawings.

Figure 2:
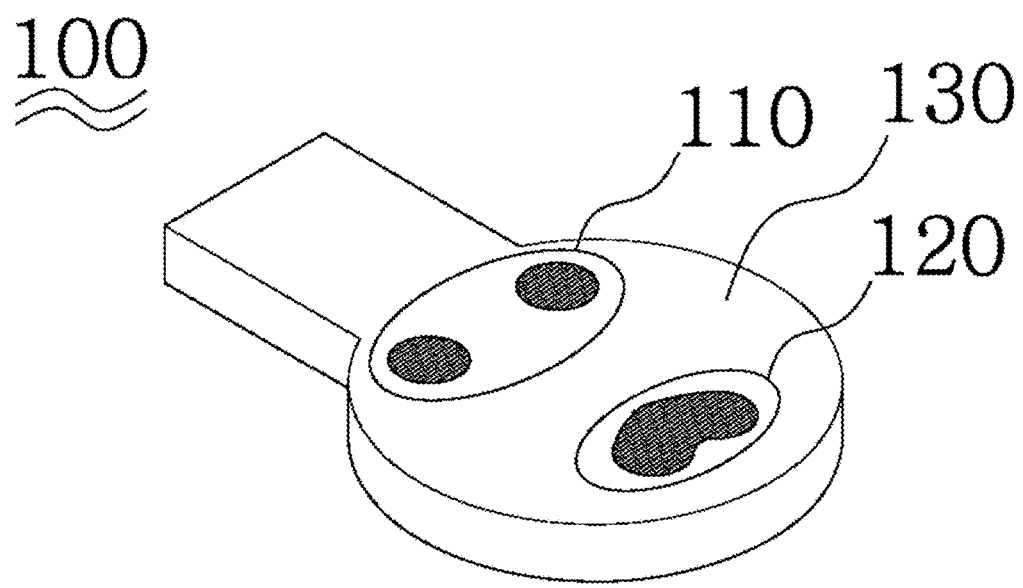
FIG. 2 schematically illustrates essential configurations of a total reflection type rain sensor using a mirror according to the present invention.
Figure 3:
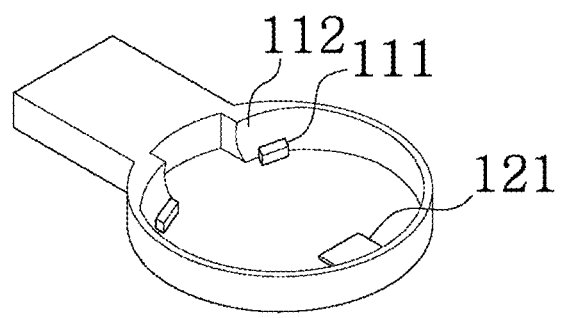
FIG. 3 schematically illustrates internal configurations of a total reflection type rain sensor using a mirror according to the present invention.
Figure 3:
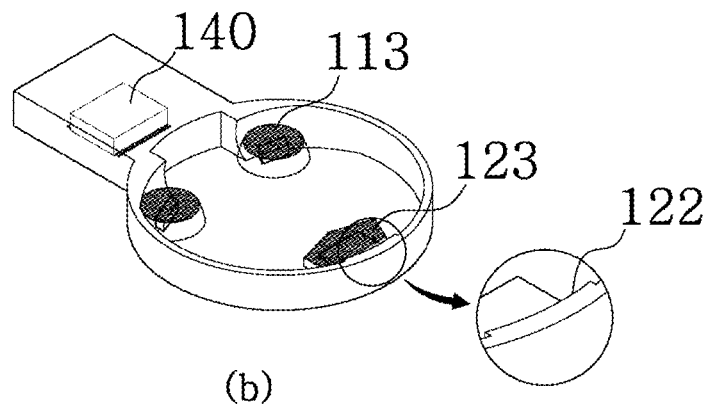

FIG. 2 schematically illustrates essential configurations of a total reflection type rain sensor using a mirror according to the present invention and FIG. 3 schematically illustrates internal configurations of a total reflection type rain sensor using a mirror according to the present invention.

The rain sensor 100 according to FIG. 2 of the accompanying drawings may comprise a light emitting unit 110, a light receiving unit 120, and an adhering portion 130.

In this case, it is preferable that the light emitting unit 110 and light receiving unit 120 of the rain sensor 100 according to the present invention are provided at a position where the light emitted from the light emitting unit 110 can be totally reflected from the glass of the vehicle and then received by the light receiving unit 120.

FIG. 3 illustrates a view (a) showing the internal configuration of the rain sensor 100 and a view (b) showing configuration in which a light emitting sawtooth-shaped rotary prism unit 113 and a light sawtooth-shaped rotary prism unit 123 are incorporated in the rain sensor 100.

As shown in FIG. 3 (a), the light emitting unit 110 may comprise a light emitting module 111 and a light emitting parabolic mirror module 112 which are provided within the rain sensor 100.

The light emitting module 111 is a means for emitting light. Although it is possible to employ various types of light sources, it is preferable to employ an infrared light source.

In addition, the light emitting module 111 may be configured to emit light to a direction toward the light emitting parabolic mirror module 112.

Figure 4:
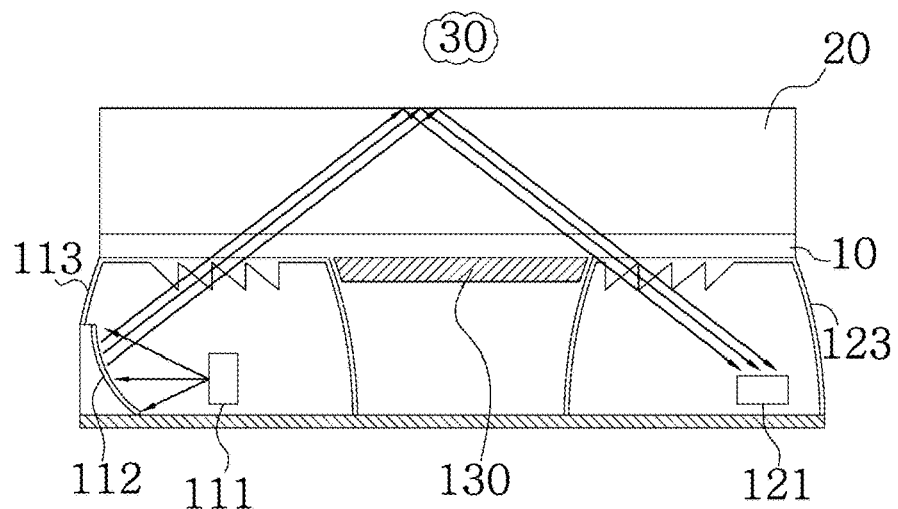
FIG. 4 illustrates schematically a movement path of light according to operation of a total reflection type rain sensor using a mirror according to the present invention.

The light emitting parabolic mirror module 112 may be configured to have a reflection surface in a paraboloidal shape as shown in FIG. 4 in order to allow the light emitted from the light emitting module 111 to reflect to a direction toward the glass of the vehicle.

In general, parallel light may be condensed through the paraboloid surface. The rain sensor according to the present invention applies such principle conversely so that the light emitted from the light emitting module 111 can be reflected in parallel through the light emitting parabolic mirror module 112.

That is, the light emitting parabolic mirror module 112 is preferably designed to have curvature of the paraboloid that allows the light emitted from the light emitting module 111 to be reflected in parallel.

In addition, the light emitting parabolic mirror module 112 may be configured such that the light emitted from the light emitting module 111 is reflected to a direction toward the glass of the vehicle and is incident at an angle that allows the light to be reflected totally from the glass of the vehicle.

The light receiving unit 120 may comprise a light receiving module 121 that functions to receive light totally reflected from the glass of the vehicle.

Referring to FIG. 3 (b), the light emitting unit 110 may further comprise a light emitting sawtooth-shaped rotary prism unit 113.

The light emitting sawtooth-shaped rotary prism unit 113 performs a function to transmit the light reflected from the light emitting parabolic mirror module 112 and is configured to accommodate surfaces of the light emitting module 111 and the light emitting parabolic mirror module 112.

The light emitting sawtooth-shaped rotary prism unit 113 may be configured such that prisms that can maintain the parallel state of light reflected from the light emitting parabolic mirror module 112 are projected toward the inner direction.

Therefore, it is possible to maintain the parallel status and an incident angle of the light reflected from the light emitting parabolic mirror module 112 by means of the light emitting sawtooth-shaped rotary prism unit 113.

This principle will be described below with reference to FIGS. 4 to 5 of the accompanying drawings.

FIG. 4 illustrates schematically a movement path of light according to operation of a total reflection type rain sensor using a mirror according to the present invention.

That is, when the light emitted from the light emitting module 111 reflects from the light emitting parabolic mirror module 112, it can has parallel wavelengths.

In this way, the light transmitting through the light emitting sawtooth-shaped rotary prism unit 113 transmits through the prisms formed in the light emitting sawtooth-shaped rotary prism unit 113 and is totally reflected from the glass 20 of the vehicle.

In this case, in order for light to be totally reflected in a specific medium, the light must be incident at an angle exceeding a threshold angle for total reflection. In this regard, the light emitting parabolic mirror module 112 in the present invention can adjust angle of light so that the light being transmitted can be incident at an angle that allows the light to be totally reflected from the glass of the vehicle.

Further, referring to FIG. 3 (b), the light receiving unit 120 may further comprise a light receiving parabolic mirror module 122 and a light receiving sawtooth-shaped rotary prism unit 123.

The light receiving parabolic mirror module 122 may have a reflective surface in a paraboloidal shape to reflect again light deviated from the light receiving module (i.e., light receiving unit) among the light totally reflected from the glass of the vehicle to the light receiving unit 121.

Figure 4A:
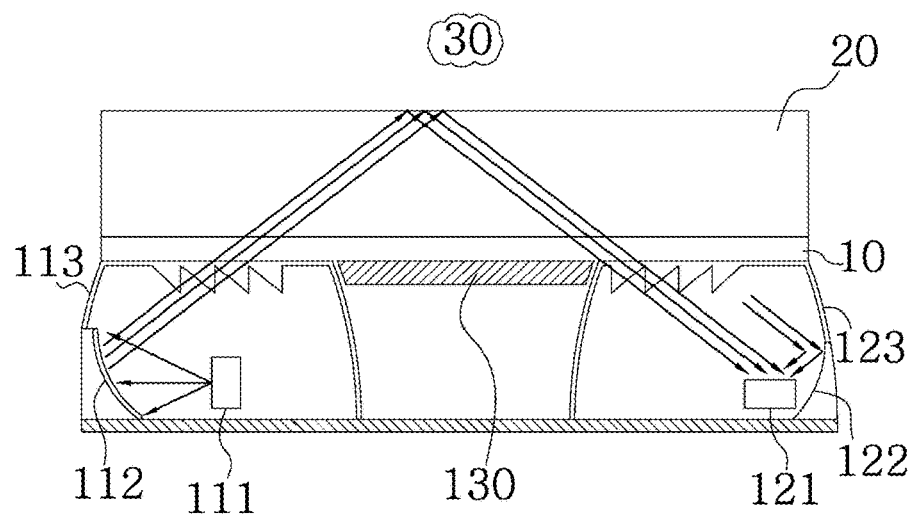
FIG. 4a illustrates schematically a movement path of light according to operation of a total reflection type rain sensor using a mirror according to another embodiment of the present invention.

In this regard, reference can be made to FIG. 4a of the accompanying drawings.

FIG. 4a illustrates schematically a movement path of light according to operation of a total reflection type rain sensor using a mirror according to another embodiment of the present invention.

That is, as an embodiment of the present invention is configured as shown in FIG. 4a of the accompanying drawings, this embodiment of the present invention is capable of receiving the light totally reflected from the glass of the vehicle more efficiently so that there is an advantage of enhancing performance of detecting raindrops.

The light receiving sawtooth-shaped rotary prism unit 123 allows the light totally reflected from the glass of the vehicle to transmit therethrough and may be configured to accommodate the light receiving module 121.

However, in case where the total reflection type rain sensor using a mirror according to the present invention comprises the light receiving parabolic mirror module 122, the light receiving sawtooth-shaped rotary prism unit 123 may be designed to accommodate surfaces of the light receiving module 121 and the light receiving parabolic mirror module 122 together.

The light receiving sawtooth-shaped rotary prism unit 123 is formed such that prisms thereof formed in a direction that is symmetrical with prisms of the light emitting sawtooth-shaped rotary prism unit 113 extend internally.

Here, the term "symmetry" can be easily understood with reference to FIGS. 4 and 4a. That is, the prisms of the light emitting sawtooth-shaped rotary prism unit are symmetrical with the prisms of the light receiving sawtooth-shaped rotary prism unit with respect to an imaginary central line in an vertical direction, not shown in the figures.

When light is totally reflected from the glass of the vehicle, the light receiving sawtooth-shaped rotary prism unit 123 deflects and guides the light to the direction toward the light receiving module 121 so that the light is received by the light receiving module.

That is, the incident light in parallel to the light receiving sawtooth-shaped rotary prism unit 123 is guided so as to transmit the prisms of the light receiving sawtooth-shaped rotary prism unit and then to be condensed at maximum to a point. Therefore, the light receiving module 121 is preferably designed to be provided in the region on which light is condensed through the prisms of the light receiving sawtooth-shaped rotary prism unit.

The principle that a total reflection type rain sensor using a mirror according to the present invention detects raindrops and an amount of the raindrops will be described with reference to FIG. 5 of the accompanying drawings.

Figure 5:
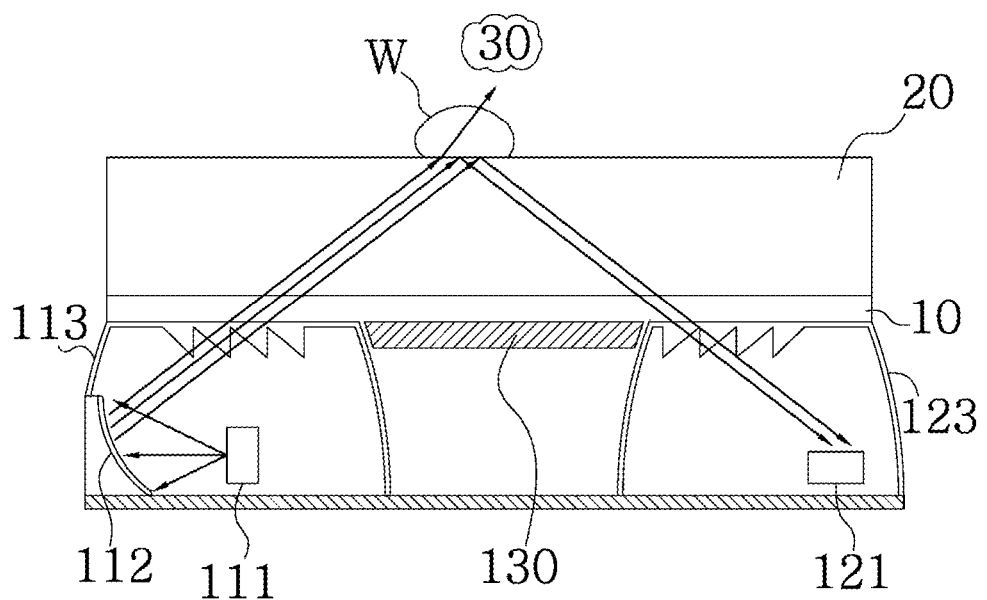
FIG. 5 illustrates schematically a movement path of light that changes as raindrops fall on the glass of the vehicle in a total reflection type rain sensor using a mirror according to the present invention.

FIG. 5 illustrates schematically a movement path of light that changes as raindrops fall on the glass of the vehicle in a total reflection type rain sensor using a mirror according to the present invention.

First, the reason why light is totally reflected from the rain sensor according to the present invention will be described with reference to FIG. 4.

In order to make total reflection occur, light must be incident from a medium of a lower refractive index to a medium of a higher refractive index and an incident angle thereof must exceed a threshold angle at which total reflection can occur.

That is, in the process of being transmitted from a medium (e.g., glass 20 of the vehicle) of a higher refractive index to a medium (e.g., air 30) of a lower refractive index as shown in FIG. 4, light must be incident at an incident angle satisfying the threshold angle.

Adjustment of the incident angle is controlled through the light emitting sawtooth-shaped rotary prism unit 113 as described above.

However, since a raindrop (i.e., water) W which is a media having a higher refractive index than air 30 is formed as shown in FIG. 5 when raindrops fall on the glass of the vehicle, the refractive index is changed by raindrops even if light is incident at a threshold angle for total reflection, and hence some light cannot but transmit or lose through raindrops, although the light that has been incident on the glass of the vehicle is reflected.

Therefore, an amount of the light received by the light receiving module 121 is necessarily smaller than that at the time when there is no raindrop W. The rain sensor 100 can detect raindrops by using such principle.

The total reflection type rain sensor using a mirror according to the present invention can be designed to have two or more detection areas. This will be described with reference to FIG. 6.

Figure 6:
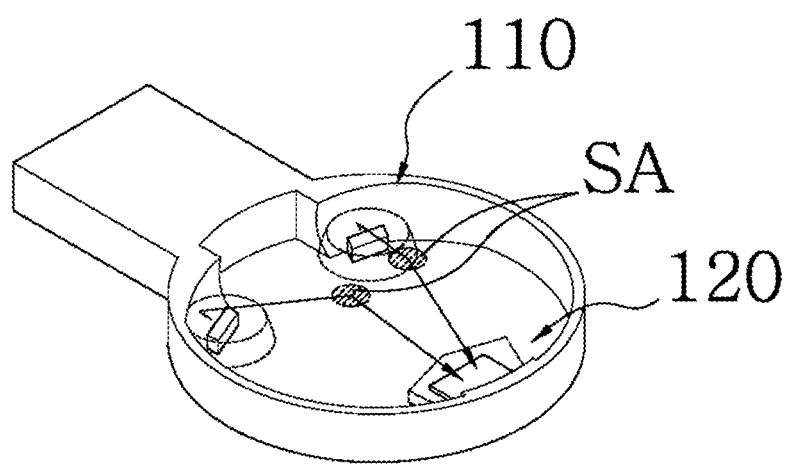
FIG. 6 is a view for explaining a detection area of a total reflection type rain sensor using a mirror according to the present invention.

FIG. 6 is a view for explaining a detection area of a total reflection type rain sensor using a mirror according to the present invention.

An example shown in FIG. 6 of the accompanying drawings is configured to have two light emitting units 110 so that it has two detection areas SA.

However, it should be understood that the scope of the present invention cannot be limited or reduced by the drawings and therefore two or more light emitting units may be composed depending on design conditions.

However, in order to facilitate understanding of the present invention, the following description will be made with reference to two light emitting units.

In addition, in case where two light emitting units 110 are provided as shown in FIG. 6, a direction of light needs to be adjusted such that the light emitted from each of the light emitting units 110 can be received by a single light receiving unit 120.

To this end, the light emitting sawtooth-shaped rotary prism unit as mentioned above is required to rotate (or adjust) the light to a direction allowing the light to be received by the light receiving unit 120 after the light transmits the light emitting sawtooth-shaped rotary prism unit and in turn it is totally reflected from the vehicle glass.

In this regard, it is noted that the term 'rotate' used herein means 'adjustment of direction' rather than 'turning about any axis.'

In this case, the light receiving unit 120 must be able to distinguish between two light beams emitted from the two light emitting units 110. For this purpose, each of the light emitting units 110 may be designed to emit light in different wavelength regions.

Accordingly, the light receiving unit 120 can distinguish which light is emitted from which light emitting unit 110 by analyzing wavelength of the light received.

However, according to other design conditions, the light receiving unit 120 may not necessarily distinguish the light emitting unit 110.

The reason is that since the light receiving unit 120 only needs to receive light and detect whether raindrops have fallen, identification of the light emitting units 110 is not necessarily required.

The adhering portion 130 allows the rain sensor 110 to be attached to the glass 20 of the vehicle.

That is, reference numeral 10 in FIGS. 4 to 5 denotes an adhesive surface bonded by the adhering portion 130. Referring to FIG. 2, the adhering portion 130 may be constructed by a means that can glue the remaining area except for areas of the light emitting sawtooth-shaped rotary prism unit 113 for allowing light to be incident on the glass of the vehicle and the light receiving sawtooth-shaped rotary prism unit 123 for receiving light.

In this case, the means that can glue the adhering portion may be a sticky material, a double-sided tape, an adhesive, or the like.

When the light receiving unit 120 detects raindrops and outputs a signal accordingly, the control unit 140 receives the signal and transmits a control signal to the vehicle by communicating with the vehicle to which the rain sensor 100 is attached.

In this case, the communication with the vehicle can be made through LIN communication.

Since the LIN (acronym of Local Interconnect Network) communication is used for data transfer between an ECU of a vehicle and an active sensor and an active actuator, it is preferable to apply to the present invention for detecting raindrops and operating the wiper of the vehicle actively.

In addition, it is possible to output the control signal for operating the wiper of the vehicle through the signal received from the light receiving unit 120.

To this end, the control unit 140 may store a predetermined threshold value for operating the wiper of the vehicle. Main functions of the control unit 140 in the present invention will be described below with reference to FIGS. 7 and 8 of the accompanying drawings.

Figure 7:
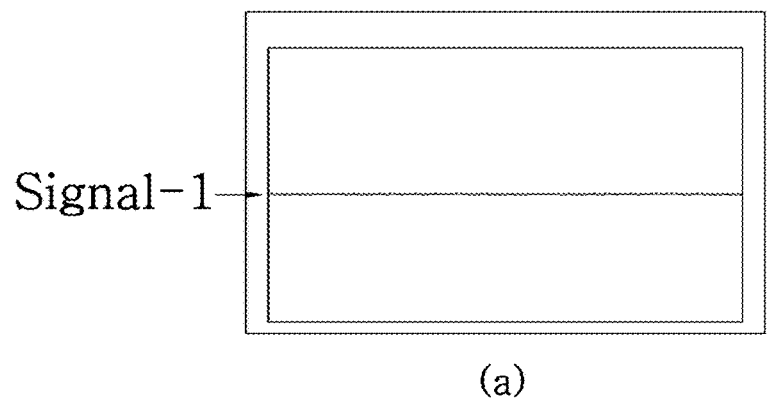
FIG. 7 is graphs plotting signals of the light receiving unit that has detected raindrops in a total reflection type rain sensor using a mirror according to the present invention.
Figure 7:
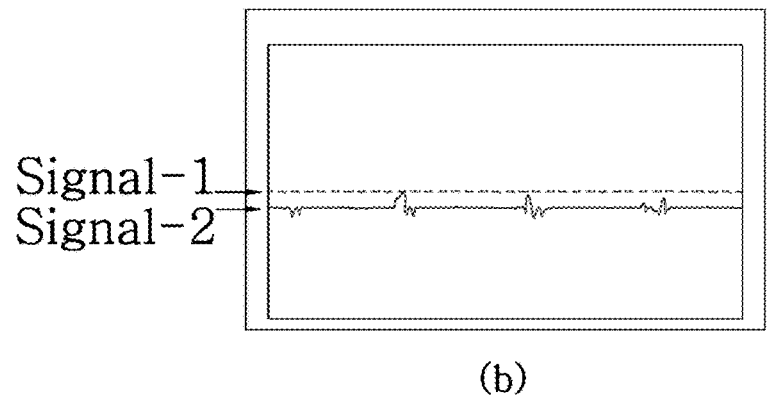
Figure 7:
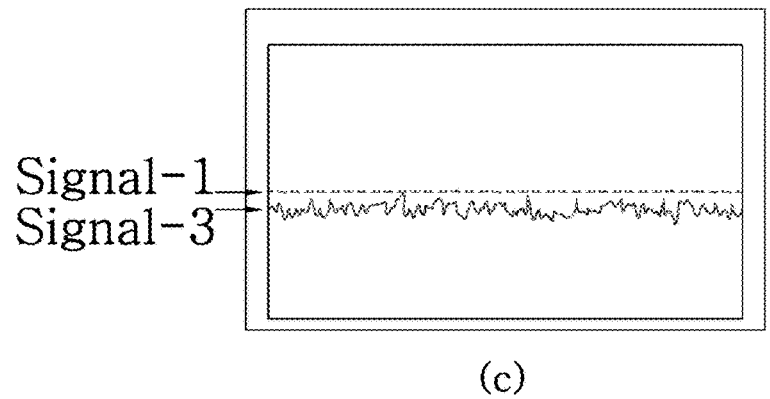
Figure 8:
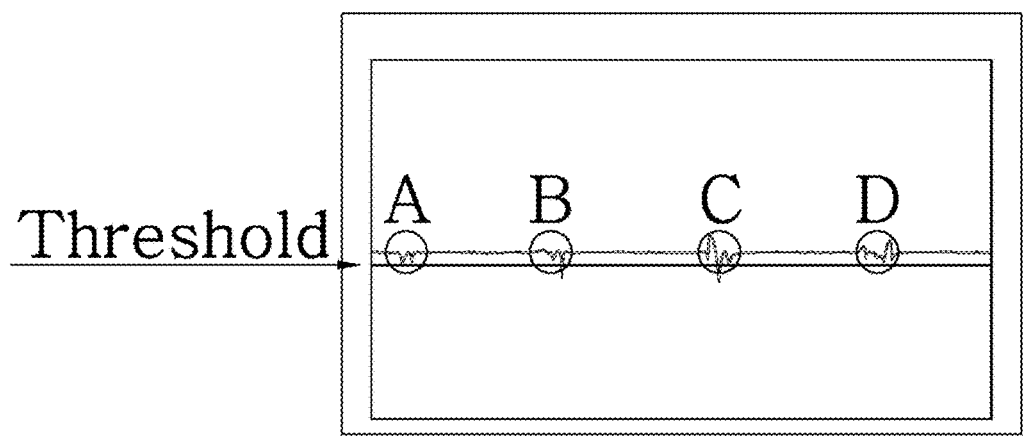
FIG. 8 is a graph illustrating a threshold value for initiating operation of a wiper according to detection of raindrops in a total reflection type rain sensor using a mirror according to the present invention.

FIG. 7 is graphs plotting signals of the light receiving unit that has detected raindrops in a total reflection type rain sensor using a mirror according to the present invention and FIG. 8 is a graph illustrating a threshold value for initiating operation of a wiper according to detection of raindrops in a total reflection type rain sensor using a mirror according to the present invention.

First, FIG. 7 illustrates a graph (a) plotting a signal output from the light receiving unit 121 when no raindrop is detected, a graph (b) plotting signals output from the light receiving unit 121 when a relatively small amount of raindrops are detected, and a graph (c) plotting signals output from the light receiving unit 121 when a large amount of raindrops are detected.

Referring to FIG. 7 (a), it can be seen that there is almost no fluctuation in the signal width because no raindrop is detected by the light receiving unit 121.

However, when a relatively small amount of raindrops are detected, the light receiving unit 121 can output a signal having a signal width varying at a regular interval as shown in FIG. 7 (b).

Here, in order to facilitate understanding of the present invention, a signal according to FIG. 7 (a) is referred to as a first signal "Signal-1", a signal according to FIG. 7 (b) is referred to as a second signal "Signal-2", and a signal according to FIG. 7 (c) is referred to as a third signal "Signal-3."

Referring to FIG. 7, the second signal Signal-2 shown in FIG. 7 (b) and the third signal Signal-3 shown in FIG. 7 (c) occur relatively below the first signal Signal-1 shown in FIG. 7 (a).

This is because when the detection area SA becomes wet due to raindrops, a signal occurs below the first signal Signal-1 at the time when there is no raindrop.

Further, the reason why a certain signal width rises upward within the region where the signal width fluctuates at a regular interval in the second signal Signal-2 is that as the wiper of the vehicle removes water from the wet detection area SA, there is a tendency to instantaneously recover the signal width at the time when there is no raindrop.

Further, when a large amount of raindrops are detected, the light receiving unit 121 can output a signal of which signal width fluctuates severely as shown in FIG. 7 (c).

However, if the wiper of the vehicle is unconditionally operated simply when the rain sensor 100 detects liquid such as raindrops on the glass of the vehicle, unnecessary power consumption is caused and an abrupt operation of the wiper may cause the driver to be surprised.

Furthermore, in case of using any product for removing water from a glass of a vehicle, or the like, which can cause raindrops falling on the glass of the vehicle to be removed by means of airflow generated during running of the vehicle, there is a possibility that raindrops fallen outside the detection area SA of the rain sensor 100 are moved to the detection area SA by the airflow generated during running of the vehicle and then detected, with the result that unnecessary operation of the wiper may be repeated. As a result, there is occurred problems that electric power is unnecessarily consumed and a safety accident may occur due to the driver's psychological change such as surprise.

Therefore, the rain sensor 100 according to the present invention is configured such that the control unit stores a predetermined threshold value for outputting a control signal to initiate operation of the wiper of the vehicle.

Reference is made to FIG. 8 of the accompanying drawings to supplement this description about the threshold.

The graph shown in FIG. 8 corresponds to a situation that the amount of raindrops detected is small. In addition, FIG. 8 indicates a threshold value.

In other words, the rain sensor 100 according to the present invention is designed such that it does not actuate the wiper unconditionally even if raindrops are detected, but outputs a control signal to initiate operation of the wiper of the vehicle only when raindrop is detected and the amount of raindrops detected exceeds the threshold value.

In this case, the threshold value indicates the minimum value of the amount of raindrops that can be a basis for initiating operation of the wiper. As an example, this will be described below with reference to FIG. 8 in which portions where the signal width varies according to detection of raindrops are divided into A, B, C and D regions.

Each of regions shows different signal widths.

That is, heights of the signal widths are different from each other because the amount of light received by the light receiving unit 121 is determined to be different depending on the amount of raindrops, wherein regions exceeding the threshold value in FIG. 8 are regions B and C.

Therefore, the rain sensor 100 according to the present invention, in the regions A and D, does not output the control signal for initiating operation of the wiper because although raindrops are detected, the amount of raindrops is determined not to reach a level that the wiper must be operated, while in the regions B and C, the rain sensor outputs the control signal for initiating operation of the wiper such that the wiper of the vehicle operates because fluctuation of the signal widths exceeds the threshold value.

In other words, the minimum value (threshold value) of the amount of raindrops for initiating operation of the wiper may be the same meaning as the minimum amount of raindrops detected by the rain sensor in order to operating the wiper.

Also, it goes without saying that in order for a user to arbitrarily change the threshold value, the rain sensor may be designed to have a user interface.

As can be seen in FIG. 7, the rain sensor configured as described above in accordance with the present invention can control cycle and/or speed of operation of the wiper of the vehicle through the control unit 140 since the amount of raindrops can be determined by means of signal.

Hereinafter, configuration of a rain sensor according to another embodiment of the present invention will be described with reference to FIG. 9 of the accompanying drawings.

Figure 9:
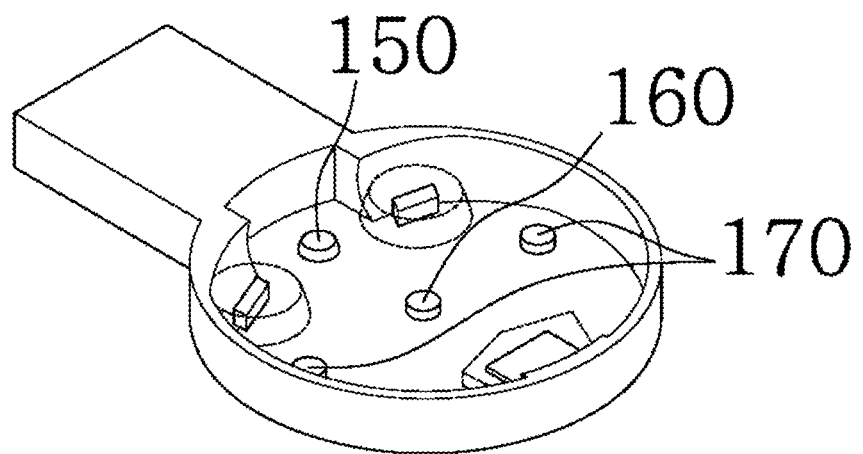
FIG. 9 schematically illustrates internal configurations of a total reflection type rain sensor using a mirror according to another embodiment of the present invention.

FIG. 9 schematically illustrates internal configurations of a total reflection type rain sensor using a mirror according to another embodiment of the present invention.

Another embodiment of the present invention further comprises an LED indicator lamp 150, an illuminance sensor 160 and a solar sensor 170, which are arranged inside the rain sensor 100. In addition, the adhering portion 130 may be provided with a lens such that the LED indicator lamp 150, the illuminance sensor 160 and the solar sensor 170 can be operated.

The LED indicator lamp 150 may be an LED lamp that displays operation of the rain sensor 100 in color. That is, it may be an indicator lamp for determining whether the rain sensor 100 is switched on or off.

The illuminance sensor 160 may function to detect illuminance of the outside of the rain sensor 100. However, when the illuminance sensor 160 is further included, the control unit 140 may control a light emission amount of infrared ray to be varied depending on illuminance detection values of the illuminance sensor 160.

Further, by identifying the day and the night based on a detection value of the illuminance sensor 160, the control unit 140 can reduce power consumption by varying a light emission intensity of infrared ray depending on the time of day and night.

The reason is that since sunray is present in the daytime, it may be necessary to adjust the light emission intensity of infrared ray depending on the time of day and night in order to minimize interference caused by infrared ray contained in the sunray.

The solar sensor 170 is provided on both sides of the rain sensor 100 and can function to detect a direction of the sun.

The total reflection type rain sensor using a mirror, configured as above in accordance with the present invention detects raindrops falling on the glass of the vehicle and outputs a control signal for initiating operation of the wiper when an amount of the raindrops exceeds a predetermined threshold value stored therein, so that unnecessary operation of the wiper can be minimized.

In addition, the present invention can enhance accuracy of deviation of the light emitting and light receiving sawtooth-shaped rotary prism units because the light emitted from the light emitting unit is reflected through the light emitting parabolic mirror module and wavelengths of the light can be reflected in parallel.

Further, the present invention can induce a more precise total reflection because when the light emitted from the light emitting unit is incident on the glass of the vehicle through the light emitting parabolic mirror module, it is possible for the light to be incident at an angle beyond a threshold angle for total reflection.

Further, the present invention can enhance accuracy of receipt of light because the light receiving sawtooth-shaped rotary prism unit is formed with prisms formed in a direction that is symmetrical with prisms of the light emitting sawtooth-shaped rotary prism unit so that (a) the light whose angle is converted can be maintained through the light emitting parabolic mirror module and (b) a direction of light can be rotated such that the light emitted from the light emitting unit can be received by a single light receiving unit.

Meanwhile, it should be noted that the foregoing description made with reference to FIGS. 1 to 9 discloses only the essential particulars of the present invention. Therefore, it is apparent that the present invention is not limited to constitutions shown in FIGS. 1 to 9 since various designs can be made within the scope of the invention.

The invention claimed is:

1. A total reflection type rain sensor using a mirror, comprising:
    a light emitting unit, wherein the light emitting unit comprises:
        a light emitting module configured to emit light;
        a light emitting parabolic mirror module having a reflective surface in a paraboloidal shape, wherein the light emitting parabolic mirror module is configured to reflect the light emitted from the light emitting module in parallel and to reflect the light to a direction of a glass of a vehicle; and
        a light emitting sawtooth-shaped rotary prism unit configured to accommodate the light emitting module and the reflective surface of the light emitting parabolic mirror module, and to transmit the light reflected from the light emitting parabolic mirror module in parallel;
    an adhering portion;
    a light receiving unit; and
    a control unit,
    wherein
    the rain sensor being attached to the glass of the vehicle to detect raindrops falling onto the glass of the vehicle,
    the light receiving unit receives light that is emitted from the light emitting unit and then reflected totally from the glass of the vehicle and outputs a signal regarding an amount of the light received; and
    the control unit outputs to the vehicle a control signal capable of initiating operation of a wiper of the vehicle in such a manner that the control unit receives and analyzes the signal of the light receiving unit and as a result of the analysis, outputs the control signal when the amount of raindrops exceeds a threshold value predetermined and stored therein.

2. The rain sensor of claim 1, wherein the light emitting parabolic mirror module reflects the light emitted from the light emitting module such that the light is incident on the glass of the vehicle at an angle that can allow the light to be totally reflected from the glass of the vehicle.

3. The rain sensor of claim 2, wherein the light receiving sawtooth-shaped rotary prism unit is formed such that prisms thereof formed in a direction that is symmetrical with prisms of the light emitting sawtooth-shaped rotary prism unit extend internally, and
    wherein when the light totally reflected from the glass of the vehicle is transmitted through the prisms, the prisms guide the light to be received therein by deviating the light toward the light receiving module.

4. The rain sensor of claim 1, wherein the light receiving unit comprises
    a light receiving module for receiving light reflected totally from the glass of the vehicle; and
    a light receiving sawtooth-shaped rotary prism unit for accommodating the light receiving module and allowing the light reflected totally from the glass of the vehicle to transmit therethrough.

5. The rain sensor of claim 4, wherein the light receiving unit further comprises a light receiving parabolic mirror module having a reflective surface in a paraboloidal shape to reflect light deviated from the light receiving unit among the light totally reflected from the glass of the vehicle to the light receiving unit, and
    wherein the light receiving sawtooth-shaped rotary prism unit accommodates reflective surfaces of the light receiving module and the light receiving parabolic mirror module.

6. The rain sensor of claim 4, wherein the light receiving sawtooth-shaped rotary prism unit is formed such that prisms thereof formed in a direction that is symmetrical with prisms of the light emitting sawtooth-shaped rotary prism unit extend internally, and
    wherein when the light totally reflected from the glass of the vehicle is transmitted through the prisms, the prisms guide the light to be received therein by deviating the light toward the light receiving module.

7. The rain sensor of claim 5, wherein the light receiving sawtooth-shaped rotary prism unit is formed such that prisms thereof formed in a direction that is symmetrical with prisms of the light emitting sawtooth-shaped rotary prism unit extend internally, and
    wherein when the light totally reflected from the glass of the vehicle is transmitted through the prisms, the prisms guide the light to be received therein by deviating the light toward the light receiving module.

8. The rain sensor of claim 1, wherein the light emitting unit comprises two or more light emitting units so that two or more detection areas for detecting raindrops exist.

9. The rain sensor of claim 1, wherein the signal of the light receiving unit is a signal regarding the amount of raindrops detected through consistent detection by the light receiving unit, and the control signal of the control unit is a signal for controlling operation, operation cycle and operation speed of the wiper of the vehicle.

10. The rain sensor of claim 1, wherein the threshold value is the minimum value of the amount of raindrops that allows operation of the wiper to initiate.

11. A total reflection type rain sensor using a mirror, comprising:
    a light emitting unit;
    an adhering portion;
    a light receiving unit, comprising:
        a light receiving module for receiving light reflected totally from the glass of the vehicle; and
        a light receiving sawtooth-shaped rotary prism unit for accommodating the light receiving module and allowing the light reflected totally from the glass of the vehicle to transmit therethrough; and
    a control unit,
    wherein
    the rain sensor is attached to the glass of the vehicle and is configured to to detect raindrops falling onto the glass of the vehicle, the light receiving unit is configured to receive light emitted from the light emitting unit and reflected totally from the glass of the vehicle and to output a signal regarding an amount of the light received; and the control unit is configured to output to the vehicle a control signal configured to initiate an operation of a wiper of the vehicle in a manner that the control unit receives and analyzes the signal of the light receiving unit and as a result of the analysis, outputs the control signal when the amount of raindrops exceeds a threshold value predetermined and stored therein.

12. The rain sensor of claim 11, wherein the light emitting unit comprises:
   a light emitting module configured to emit light;
   a light emitting parabolic mirror module having a reflective surface in a paraboloidal shape, wherein the light emitting parabolic mirror module is configured to reflect the light emitted from the light emitting module in parallel and to reflect the light to a direction of a glass of a vehicle; and
   a light emitting sawtooth-shaped rotary prism unit configured to accommodate the light emitting module and the reflective surface of the light emitting parabolic mirror module, and to transmit the light reflected from the light emitting parabolic mirror module in parallel.

13. The rain sensor of claim 12, wherein the light emitting parabolic mirror module is configured to reflect the light emitted from the light emitting module such that the light is incident on the glass of the vehicle at an angle that allow the light to be totally reflected from the glass of the vehicle.

14. The rain sensor of claim 11, wherein the light receiving unit further comprises a light receiving parabolic mirror module having a reflective surface in a paraboloidal shape to reflect light deviated from the light receiving unit among the light totally reflected from the glass of the vehicle to the light receiving unit, and
   wherein the light receiving sawtooth-shaped rotary prism unit accommodates reflective surfaces of the light receiving module and the light receiving parabolic mirror module.

15. The rain sensor of claim 14, wherein the light receiving sawtooth-shaped rotary prism unit is formed such that prisms thereof formed in a direction that is symmetrical with prisms of the light emitting sawtooth-shaped rotary prism unit extend internally, and
   wherein when the light totally reflected from the glass of the vehicle is transmitted through the prisms, the prisms guide the light to be received therein by deviating the light toward the light receiving module.

16. The rain sensor of claim 11, wherein the light receiving sawtooth-shaped rotary prism unit is configured such that prisms thereof formed in a direction that is symmetrical with prisms of the light emitting sawtooth-shaped rotary prism unit extend internally, and
   wherein when the light totally reflected from the glass of the vehicle is transmitted through the prisms, the prisms guide the light to be received therein by deviating the light toward the light receiving module.

17. The rain sensor of claim 11, wherein the light emitting unit comprises two or more light emitting units so that two or more detection areas for detecting raindrops exist.

18. The rain sensor of claim 11, wherein the signal of the light receiving unit is a signal regarding the amount of raindrops detected through consistent detection by the light receiving unit, and the control signal of the control unit is a signal for controlling operation, operation cycle and operation speed of the wiper of the vehicle.

19. The rain sensor of claim 11, wherein the threshold value is the minimum value of the amount of raindrops that allows operation of the wiper to initiate.

20. The rain sensor of claim 11, wherein the light receiving sawtooth-shaped rotary prism unit is formed such that prisms thereof formed in a direction that is symmetrical with prisms of the light emitting sawtooth-shaped rotary prism unit extend internally, and
   wherein when the light totally reflected from the glass of the vehicle is transmitted through the prisms, the prisms guide the light to be received therein by deviating the light toward the light receiving module.

* * * * *